United States Patent
Meurer et al.

(10) Patent No.: US 11,692,945 B2
(45) Date of Patent: Jul. 4, 2023

(54) APPARATUS AND METHOD FOR DETECTING AND SAMPLING DISSOLVED HYDROCARBONS

(71) Applicant: ExxonMobil Technology and Engineering Company, Spring, TX (US)

(72) Inventors: William P. Meurer, Magnolia, TX (US); Michael G. Braun, Houston, TX (US)

(73) Assignee: ExxonMobil Technology and Engineering Company, Spring, TX (US)

( * ) Notice: Subject to any disclaimer, the term of this patent is extended or adjusted under 35 U.S.C. 154(b) by 357 days.

(21) Appl. No.: 16/947,722

(22) Filed: Aug. 13, 2020

(65) Prior Publication Data
US 2021/0055231 A1    Feb. 25, 2021

Related U.S. Application Data (60) Provisional application No. 62/888,598, filed on Aug. 19, 2019.

(51) Int. Cl.
*G01N 21/94* (2006.01)
*G01N 1/10* (2006.01)
*G01N 33/18* (2006.01)

(52) U.S. Cl.
CPC .............. *G01N 21/94* (2013.01); *G01N 1/10* (2013.01); *G01N 33/1833* (2013.01)

(58) Field of Classification Search
CPC ...... G01N 21/94; G01N 1/10; G01N 33/1833; G01N 2001/1056
See application file for complete search history.

(56) References Cited

U.S. PATENT DOCUMENTS

| | | | |
|---|---|---|---|
| 6,187,530 B1 | 2/2001 | Scholin et al. | |
| 8,215,164 B1 * | 7/2012 | Hussain | E21B 43/14 |
| | | | 73/152.33 |
| 9,146,225 B2 | 9/2015 | Pottorf et al. | |
| 9,453,828 B2 | 9/2016 | Corbett et al. | |
| 9,612,231 B2 | 4/2017 | Pottorf et al. | |
| (Continued) | | | |

FOREIGN PATENT DOCUMENTS

| | | | | |
|---|---|---|---|---|
| GB | 2246082 A * | 1/1992 | ............... | G01N 1/10 |
| GB | 2246082 A | 1/1992 | | |

OTHER PUBLICATIONS

ASTM International Designation: D4489-95 (2011) Standard Practices for Sampling of Waterborne Olls, 4pgs.
(Continued)

*Primary Examiner* — David Z Huang
(74) *Attorney, Agent, or Firm* — Lempia Summerfield Katz LLC (57) ABSTRACT

Detection and sampling of dissolved hydrocarbons of interest in an environment expected to have hydrocarbon molecules, such as a water column or interstitial water in sediment. An apparatus comprising at least one oleophilic film frame is deployed into the environment and the at least one oleophilic film frame is exposed thereto for a defined period of time, and thereafter isolated from the environment to cease exposure thereto. Hydrocarbon molecules scavenged by the oleophilic film may be analyzed to determine their type and/or concentration.

16 Claims, 2 Drawing Sheets

(56) References Cited

U.S. PATENT DOCUMENTS

| | | | |
|---|---|---|---|
| 9,638,828 B2 | 5/2017 | Levien et al. | |
| 9,802,183 B2 * | 10/2017 | Hanby | G01N 33/1833 |
| 9,829,602 B2 | 11/2017 | Bond et al. | |
| 2010/0068821 A1 * | 3/2010 | St. Germain | G01N 33/1826 436/140 |
| 2015/0224502 A1 | 8/2015 | Pargett | |
| 2017/0299502 A1 * | 10/2017 | Schanzer | G01N 21/94 |
| 2018/0088008 A1 | 3/2018 | Ghosh et al. | |

OTHER PUBLICATIONS

Bell (2007) "Calibration of an In Situ Membrane Inlet Mass Spectrometer for Measurements of Dissolved Gases and Volatile Organics in Seawater", Environmental Science & Technology, vol. 41, No. 23, pp. 8123-8128.

Caccia, M. et al. (2005) "An Autonomous Craft for the Study of Sea-Air Interactions: Sampling Sea Surfaces with SESAMO", IEEE Robotics & Automation Magazine, pp. 95-105.

Camilli, R. et al. (2007) "Characterizing marine hydrocarbons with in-situ mass spectrometry", MTS, 7pgs.

Camilli, R. et al. (2009) "Characterizing Spatial and Temporal Variability of Dissolved Gases in Aquatic Environments with in situ Mass Spectrometry", Environmental Science & Technology, vol. 43, No. 13, pp. 5014-5021.

Camilli, R. et al. (2010) "Tracking Hydrocarbon Plume Transport and Biodegradation at Deepwater Horizon", Science, vol. 330, Oct. 8, 2010, pp. 201-204.

Camilli, R. et al. (2004) "Integrating In-situ Chemical Sampling with AUV Control Systems", IEEE, pp. 101-109.

Camilli, R. et al. (2009) "Method for rapid localization of seafloor petroleum contamination using concurrent mass spectrometry and acoustic positioning", Marine Pollution Bulletin, vol. 58, pp. 1505-1513.

C-Cat 5 Specification (2014) Multipurpose Work USV, Autonomous Surface Vehicles Ltd (ASV) unmanned marine systems, 2pgs.

Chase, C. R. et al. (2010) "Real-Time Monitoring of Oil Using Ultraviolet Filter Fluorometry: Slick Sleuth, Slick Guard Employ Noncontact Fluorescence Sensors for Autonomous Oil Slick Detection", www.sea-technology.com, Oct. 2010, pp. 45-49.

Dagleish, F. R. et al. (2013) "Towards Persistent Real-Time Autonomous Surveillance and Mapping of Surface Hydrocarbons", OTC 24241, Offshore Technology Conference, Houston, TX, USA, May 6-9, 2013, pp. 1-18.

Fries, D. et al. (2011) "Solar Robotic Material Sampler System for Chemical, Biological and Physical Ocean Observations", MTS, 5pgs.

Jakuba, M. V. et al. (2011) "Toward Automatic Classification of Chemical Sensor Data from Autonomous Underwater Vehicles", 2011 IEEE/RSJ International Conference on Intelligent Robots and Systems, Sep. 25-30, 2011, San Francisco, CA, USA, pp. 4722-4727.

Kinsey, J. C. et al. (2011) "Assessing the Deepwater Horizon Oil Spill with the Sentry Autonomous Underwater Vehicle", 2011 IEEE/RSJ International Conference on Intelligent Robots and Systems, Sep. 25-30, 2011, San Francisco, CA, USA, pp. 261-267.

Lamontagne, R. A. et al. (2001) "Response of METS Sensor to Methane Concentrations Found on the Texas-Louisiana Shelf in the Gulf of Mexico", Naval Research Laboratory, Washington, DC 20375, NRL/MR/6110-01-8584, Oct. 15, 2001, 14pgs.

Tedetti, M. et al. (2010) "Utilization of a submersible UV fluorometer for monitoring anthropogenic inputs in the Mediterranean coastal waters", Marine Pollution Bulletin, vol. 60, pp. 350-362.

UV-AquaTracka, In-situ Hydrocarbon Fluorometer, Chelsea Technologies Group Ltd. (2014), Surrey, United Kingdom, 2pgs.

Zhang, Y. et al. (2011) "A Peak-Capture Algorithm Used on an Autonomous Underwater Vehicle in the 2010 Gulf of Mexico Oil Spill Response Scientific Survey", Journal of Field Robotics, vol. 28, No. 4, pp. 484-496.

* cited by examiner

APPARATUS AND METHOD FOR DETECTING AND SAMPLING DISSOLVED HYDROCARBONS

CROSS REFERENCE TO RELATED APPLICATION

This application claims the benefit and priority of U.S. Provisional Application Ser. No. 62/888,598, filed Aug. 19, 2019 the disclosure of which is incorporated herein by reference in its entirety.

FIELD

The present disclosure relates to the detection and sampling of dissolved hydrocarbons and apparatus and methods related thereto.

BACKGROUND

Detection of hydrocarbon liquid components, particularly those dissolved in water (e.g., released into ocean settings from natural seepage) may be difficult due to their low solubility and/or due to substantial dilution. There are currently two strategies for detecting hydrocarbons in such bodies of water, including in situ measurement and water sampling followed by laboratory analyses. In situ technologies are challenged by certain detection limits; for example, underwater mass spectrometers have detection limits of about 5-10 parts per billion (ppb) or higher for molecules with masses in the most desirable detection ranges, such as benzene and/or toluene. Underwater fluorometers are more sensitive, but are themselves challenged, such as because hydrocarbon fluorescence intensity is inversely correlated with solubility in water. For example, relatively fluorescent four ring aromatic compounds have a maximum solubility of only about 100 ppb. Such compounds can, accordingly, undergo at most 3 to 4 orders of magnitude dilution from a saturated solution before they are no longer detectable (e.g., for detection limits of about 50-100 parts per trillion (ppt)).

An alternate detection strategy that has previously been used for measuring background concentrations of hydrocarbon compounds of interest is to deploy passive collectors. Such passive collectors employ material that has a strong affinity for target compounds of interest and, if deployed underwater, the material is typically hydrophobic. This strategy uses long exposure times to accumulate target compounds that are later analyzed after the material is recovered in a laboratory environment, and may be referred to in the industry as "drop and collect" strategies. The resulting detection capability can correspond to an effective detection equivalent of less than about 5-50 ppt, depending on the material used, deployment time, and analysis technique.

It is desirable to have a hydrocarbon sampling apparatus and method that is tailored to a particular compound or compounds of interest, tailored to a particular environment in which such compound is being sampled, and takes advantage of the time-integration uplift of passive sampling.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to the detection and sampling of dissolved hydrocarbons and apparatus and methods related thereto.

It may be difficult to detect dissolved hydrocarbons in a water source, such as leakage from a pipeline, natural seepage, and/or production facility leakage. Nevertheless, knowledge of the presence of such sources of hydrocarbons may be of great value to the petroleum industry. Knowledge of some hydrocarbon sources may be of less value to the petroleum industry compared to others. For example, biogenic hydrocarbon sources are produced as a direct consequence of bacterial activity and are overwhelmingly (e.g., ≥99%) methane. Typically, biogenic hydrocarbons are of less value compared to thermogenic hydrocarbons, especially those from biogenic sources that are broadly distributed, which are produced under conditions of high temperature and pressure. Biogenic and thermogenic hydrocarbons may be distinguished on the basis of chemical and carbon isotopic composition.

Prior use of passive sampling techniques have been limited due to various challenges, and may only provide a time-weighted average of a particular water source environment. Passive sampling, however, is advantageous in that it is typically easy to perform, can be employed in a wide range of environments, and can effectively concentrate target molecules compared to active sampling. Active sampling techniques advantageously provide a snapshot of a water source environment at a particular location and time, but may be limited in their usefulness for identifying low concentration hydrocarbon sources. Differently, the embodiments of the present disclosure employ a single-exposure or multiple-exposure hydrocarbon sampler capable of exposing a film of oleophilic material for a particular period of time and, thereafter, isolating such film and, in the case of the multiple-exposure sampler, exposing a new film frame.

It is to be noted that although the present disclosure describes the samplers of the present disclosure primarily with reference to multiple-exposure samplers, single-exposure samplers are also contemplated and are within the scope of the present disclosure. Moreover, it is to be noted that although the present disclosure describes the samplers of the present disclosure primarily with reference to sampling a water source (e.g., a seabed seepage area, particularly with detectable or elevated methane), sampling of other environments is also contemplated and are within the scope of the present disclosure. For example, the samplers of the present disclosure may be utilized to sample soft sediment (e.g., interstitial water in sediment) locations for oil seepage. Moreover, the samplers described herein may be utilized for environmental monitoring for baseline assessment of hydrocarbons or facilities/pipeline hydrocarbon leakage.

The samplers described herein are advantageously both passive and active by exposing a passive sampling material during a defined period of time that is able to provide a snapshot of a particular water source environment. The samplers may be referred to herein as "oil cameras," which expose oleophilic film and, thereafter, isolates said film, and may further advance the film to a subsequent frame.

As used herein, the term "hydrocarbon," and grammatical variants thereof, refers to a compound primarily of hydrogen and carbon, the compound having at least six carbon atoms; the term "oleophilic," and grammatical variants thereof, refers to a material having an affinity for such hydrocarbons.

When in use, the oil camera of the present disclosure exposes at least one frame of oleophilic film for a period of time. The period of time may be pre-defined, or alternatively manipulated on the fly, either by manual operation or control by one or more sensors providing input to the oil camera. The particular time period may depend on a number of factors including, but not limited to, the concentration (including fluctuation of the concentration) of methane or higher hydrocarbons being exposed to the film, the type of film selected and its detection limits, the type of deployment platform selected, the on-site time available, and the like, and any combination thereof. In any or all embodiments, the exposure period of time may be in the range of about one hour to about two weeks, encompassing any value and subset therebetween.

In any or all embodiments, the oil camera may be configured to receive input directly or indirectly from a sensor, such as a methane sensor (also referred to in the industry as a "methane detector"). That is, the oil camera may be in electrical communication with the methane sensor (and/or other detection sensor, as described herein), the oil camera may receive input from a digital processor that receives input from the methane sensor, and/or the methane sensor may ultimately provide readings to an operator that manually operates the oil camera. The presence of methane in a particular location may be directly correlated to the presence of hydrocarbon molecules, as defined herein, in the same or adjacent location. That is, the presence of methane may indicate the presence of hydrocarbon molecules, and as the concentration of methane increases, the concentration of hydrocarbon molecules may also increase. Accordingly, the film exposure time may be controlled based on an inference of the likely concentration of hydrocarbon molecules gleaned from the methane concentration provided by the methane sensor. After the exposure time has elapsed, the exposed film frame may be isolated (e.g., by closing a shutter opening, by advancing the exposed film into isolation, and the like), and optionally a new film frame may be exposed at a subsequent time thereafter. In some embodiments, the film frame, the exposure, and isolation of the oleophilic film frames described herein may be based on a pre-defined period of time, controlled manually (e.g., by an operator), and/or triggered directly or indirectly from input or command by the methane sensor. Indirect control of the film exposure may be based on a sensor achieving a threshold value for a specified period of time. For example, if an associated methane sensor measures at least 150 ppt for at least one minute, or 300 ppt for at least 30 seconds, exposure of a film frame may be triggered (e.g., by advancing a film frame to be exposed to an environment or by triggering a shutter to open. Indirect control may also include a specific threshold value, such as when the methane sensor detects 500 ppt. In another embodiment, indirect control may be based on multiple sensors that combine to define a trigger value, or otherwise control exposure of the film; for example, if the methane sensor is more than 100 ppt and a fluorometer is more than 70 ppt, with readings occurring in coincident acquisition intervals, then exposure may be triggered.

The oleophilic film for use in the oil camera of the present disclosure may be any material capable of scavenging hydrocarbon molecules from an environment, such as a water source. The effectiveness of the scavenging capability of the oleophilic film may be based on a number of factors, including, but not limited to, the type of film used, the physical characteristics of the film used (e.g., surface roughness), the size and thickness of the film used, the exposure time, the rate at which any depleted boundary layer near the film can be replenished, and the like, and any combination thereof. Moreover, depending on the type of film, certain processing techniques may be more or less effective for recovering the scavenged hydrocarbon molecules from the film. For example, a film may be particularly effective at scavenging hydrocarbon molecules, but be chemically similar thereto, thus requiring additional post-analysis steps to further distinguish between the film and the hydrocarbons. In another example, the film may be particularly effective at scavenging hydrocarbon molecules, but lack mechanical properties to withstand certain desorption post-analysis methods. Accordingly, the type of film selected may also depend on the desired post-analysis method (e.g., based on the compatibility with the hydrocarbons or film, based on the availability of equipment, and the like).

The film may be segmented such that it is comprised of a plurality of frames, and each frame is isolated from adjacent frames by a boundary or barrier that prevents diffusion (or bleeding) of compounds between the frames. In other embodiments, each frame may be physically detached or otherwise cut away from a reel of film (e.g., by use of a mechanism within the oil camera) to prevent diffusion of compounds between frames. In still other embodiments, the oil camera may be configured such that an area of the film frame is exposed and, thereafter, advanced sufficiently such that an area of non-exposure bounds the perimeter of the exposed portion, thereby preventing diffusion of compounds between frames. In other embodiments, a layer of isolation material may be spooled between exposed film frames to prevent diffusion. Other configurations to prevent diffusion of compounds between frames are also contemplated and are within the scope of the present disclosure.

The physical format of the film is flexible, and may be in the form of a linear array of frames (i.e., similar to photographic film), a sheet of frames forming a two-dimensional array of frames, or a stacked three-dimensional array of frames. The oil camera may be configured to accept only one type of film format, or may be configured to accept one or more, including all, types of film format. The oil camera may be configured to expose only a single frame during a particular period of time (pre-defined or otherwise) to provide controlled exposure of a single sample during exposure time. Alternatively, the camera may be configured to allow temporally overlapping exposure of two or more frames, thereby allowing temporal or spatial variations in target molecule concentrations to be resolved.

The size and thickness of each film frame may be maximized to effectively scavenge desired hydrocarbon molecules. Typically, the film's area is relatively large and the film's thickness is relatively thin. In any or all embodiments, the size of the film may be in the range of about 4 square centimeters (cm$^2$) to about 650 cm$^2$, encompassing any value and subset therebetween. In any or all embodiments, the thickness of the film may be in the range of about 25 micrometers (μm) to about 250 μm, encompassing any value and subset therebetween.

Examples of suitable material for use as the oleophilic film of the oil camera described herein may include, but is not limited to, polydimethylsiloxane (PDMS), poly(imino (1,6-dioxo-1,6-hexanediyl)imino-1,6-hexanediyl) (Nylon 6,6), woven polytetrafluoroethylene (PTFE), polypropylene cloth, polyethylene, low-density polyethylene, and the like, and any combination thereof. In some embodiments, a single suitable material is used to form the oleophilic film. In other embodiments, more than one material may be used to form the oleophilic film (e.g., wherein two or more materials are positioned next to each other, or on separate sides of the oleophilic film). The selection of the particular material for use as the oleophilic film may depend on a number of factors including, but not limited to, the material's scavenging ability, the type of hydrocarbon(s) being scavenged, the post-analysis technique(s) selected, and the like, and any combination thereof.

In any or all embodiments, the type of oleophilic film selected may be calibrated to recover a detectable hydrocarbon signal as a function of the exposure duration and the average concentration (e.g., in-water concentration) of hydrocarbons. As such, the exposure period of time may be manipulated. For example, a detection limit of 100 ppt may require that the oleophilic film selected is exposed for a period of time of about 30 minutes for certain concentrations of hydrocarbons, whereas a detection limit of 10 ppt might require a greater amount of time for the same concentration of hydrocarbons (e.g., about five hours). As discussed herein, film type, film size (e.g., area), film thickness, and exposure type (e.g., active use of a pump to flow water through or over the film) may be adjusted to maximize or optimize the required exposure time and mass of hydrocarbons to be recovered.

In any or all embodiments, after exposure to an actual or predicted hydrocarbon-rich water column area, the film may be treated to minimize degradation of the accumulated hydrocarbons, such as with a biocide. The biological-control may be integral to the film, or it may be introduced after exposure of the film. For example, a biocide may be included as a distributed surface coating on the film, or in strips incorporated into the film's structure (e.g., copper strips). The biological-control may be introduced after exposure of the film, such as by including biocides, pH changes, exposure to copper, limiting access to water, and other chemical and physical strategies suited to the exposed film storage volume. Such biocide treatment may, for example, be housed within the oil camera. For example, once the exposed film frame is isolated (optionally while another frame is advanced), the already exposed film frame may be coated or otherwise treated with an anti-degradation chemical. In any or all embodiments, for instance, the previously-exposed film may advance through one, or a pair of rollers (e.g., squeeze rollers), that transfers the anti-degradation chemical to the film, or may be advanced into a cartridge that comprises the anti-degradation chemical for which the film may be stored prior to processing.

Exposed film frames may be analyzed to determine the type and amount of hydrocarbons located in a particular water source. As described in greater detail hereinbelow, various non-destructive and/or destructive post-analysis techniques may be used including, but not limited to: fluorescence analysis, thermal desorption, chemical desorption, flame detection, gas chromatograph mass spectrometry (GC-MS), gas chromatograph tandem mass spectrometry (GC-MS/MS), gas chromatography with flame-ionization detection (GC-FID), and the like, and any combination thereof. Moreover, depending on the post-analysis technique selected, real or substantially real time analysis may be performed after a frame is exposed. For example, an on-board system (e.g., fluorescent microscope or spectrometer) may be used to provide a real or substantially real time assessment of the effectiveness of the exposure in capturing hydrocarbon molecules. Such information may be used to adjust parameters of exposure for the next (or another) film frame (e.g., length of time of exposure), and/or whether the next film frame should be exposed in the same location, for example.

The structure of the oil camera described herein is not considered to be particularly limited, provided that the oleophilic material may be exposed and then isolated within a determined period of time. In one or all embodiments, for example, the oil camera apparatus comprises at least a housing and a film advance system integrated with the housing. The film advance system may be configured to advance the first frame into an opening (e.g., to expose the film). Accordingly, the film advance system may form a portion of the housing, or otherwise be disposed within the housing in some embodiments, or the film may be advanced, or otherwise manipulated in whole or in part, by a film advance system that is not otherwise a component of the oil camera. Optionally, the oil camera apparatus further comprises a control system configured to control the film advance system. Optionally, the oil camera apparatus further comprises a shutter system disposed within the housing, the shutter system comprising: a shutter opening through which a first frame of oleophilic film is exposed, and a shutter blade configured to move the shutter opening between an open position, to expose both the shutter opening and the first frame, and a closed position to cover the shutter opening. The film advance system may advance the film into or otherwise through the shutter opening to expose the film. In any or all further embodiments, the optional control system may be configured to control only the shutter system, or both of the shutter system and the film advance system.

Various configurations of the oil camera are contemplated in one, more, or all of the embodiments described herein. For example, the oil camera may be configured such that the control system is able to remotely control one or both of the shutter system and/or the film advance system. In such cases, for instance, a remote operator may be able to operate the oil camera while it is located in a marine environment (e.g., on a seabed) or in another water column, without the operator being physically in contact with the housing or another element of the oil camera. As used herein, a "marine environment" refers to a water associated with the sea, excluding lacustrine and fresh-water channel water settings. Conversely, it is contemplated that the oil camera may be operated by physical contact with the oil camera, as well. For example, the control system may comprise a film advance reel or knob that when deployed advances a film frame into an opening for exposure to an environment and, when further rotated (or otherwise progressed), isolates the film frame and, optionally, exposes a subsequent film frame; in additional or alternative embodiments, the control system may comprise a shutter-release button that when deployed opens the shutter opening and, when no longer deployed, closes the shutter opening, thereby isolating the previously exposed film frame.

Isolating exposed film frames may be of significance in order to ensure that the oleophilic film retains the hydrocarbons of interest. That is, the oleophilic material is able to scavenge and retain hydrocarbons, but such retention is based upon equilibrium partitioning. If the oleophilic film materials described herein are allowed to equilibrate with water content that has a lower hydrocarbon content than that previously experienced by the film, the scavenged hydrocarbons will desorb from the oleophilic material. Initial equilibration times will be specific and known for each oleophilic material for various hydrocarbon molecules of interest. For at least these reasons, it is additionally not recommended that the film be exposed longer than required to measure the concentration of the compound(s) of interest.

Accordingly, careful observation of the hydrocarbon content of a water source of interest is important (e.g., by use of a methane sensor) and the ability to isolate an unexposed and exposed film frame is also important. In one or all embodiments, a fluid-tight, or severely restrictive, seal is formed within the housing to isolate unexposed and exposed film (e.g., the shutter blade in its closed position (i.e., covering the shutter opening) is configured to form a fluid-tight seal of the shutter opening). As such, control of the type and amount of hydrocarbons absorbed onto a film can be achieved and, an exposed film frame may be isolated to prevent, any hydrocarbon desorption into the surrounding water environment. The mechanism of forming the fluid-tight seal is not considered to be particularly limiting and may employ, for example, a gasket or other sealing material that prevents leakage to the exposed film within the housing of the oil camera. The film advance system may also participate in isolating the exposed film.

The film advance system may be any mechanism capable of advancing the oleophilic film within the housing of the oil camera and further isolating the exposed film, including in some embodiments beyond merely the fluid-tight seal formed by the housing or closed shutter blade, thereby allowing exposure of one or more subsequent film frames, while maintaining the already exposed frame in isolation. The film advance system may have one or more moving parts to achieve advancement of the film. In any or all embodiments, for example, the film advance system may be in the form of a film carrousel or a film spool (e.g., a two-spool or more system for advancing the film frames). In embodiments having multiple film frames for use in the oil camera of the present disclosure, the film advance system may be configured to advance and isolate a first exposed film frame and, thereafter, position a second film frame within the shutter opening for later exposure. Positioning of the second film frame may be after, or simultaneous with, advancement and isolation of the exposed first film frame. In this manner, a plurality of film frames may be separately exposed and each isolated from the surrounding environment and, in some instances, also from adjacent exposed frames. Isolation from adjacent frames may be achieved, for example, by utilizing a film backing or isolating material that prevents diffusion, such that the exposed film frames may be rolled onto a spool and the film backing prevents contact between each of the rolled frames.

Further, in any or all embodiments, a control system (e.g., a drive mechanism, spring, electrical mechanism, electromechanical mechanism, and the like) may be utilized to operate one or both of the film advance system and optionally the shutter system. The control system may be any of a mechanical, electrical, pneumatic, hydraulic, or other suitable mechanism for allowing at least one film frame of an oil camera described herein to be exposed and, thereafter, again isolated in an environment of interest. In some instances, the control system is further configured to ensure that the film frame is isolated prior to exposure to the environment of interest.

In some instances, the control system may operate the film advance system such that once the film advance system is activated to advance exposed film, it may trigger the shutter blade to open and expose a new oleophilic film frame. That is, the film advance system may be configured to move the shutter blade between its open and closed position under control of the control system. Conversely, the shutter system may be configured such that once the shutter blade is closed, an exposed film frame is automatically advanced by the film advance system to isolate the exposed film frame.

Figure 1A:
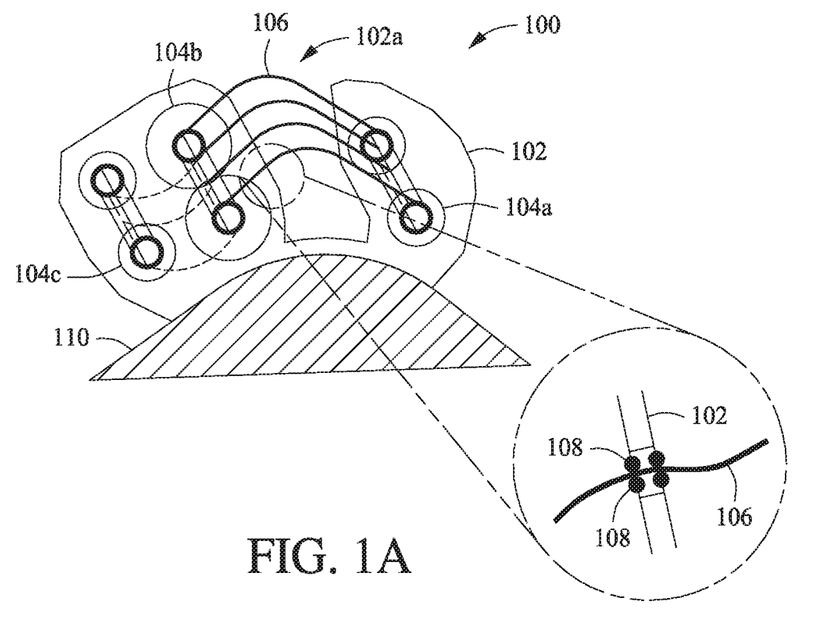
FIG. 1A is an embodiment of an oil camera comprising a housing, a film advance system, and a control system, in accordance with one or more embodiments of the present disclosure.
Figure 2A:
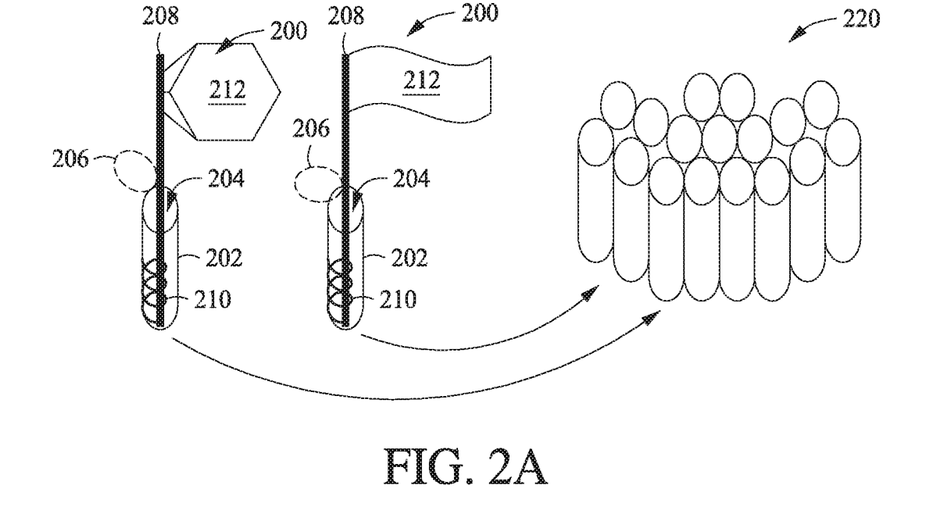
FIG. 2A is an embodiment of an oil camera comprising a housing, a film advance system, a shutter system, and a control system, in accordance with one or more embodiments of the present disclosure.
Figure 2B:
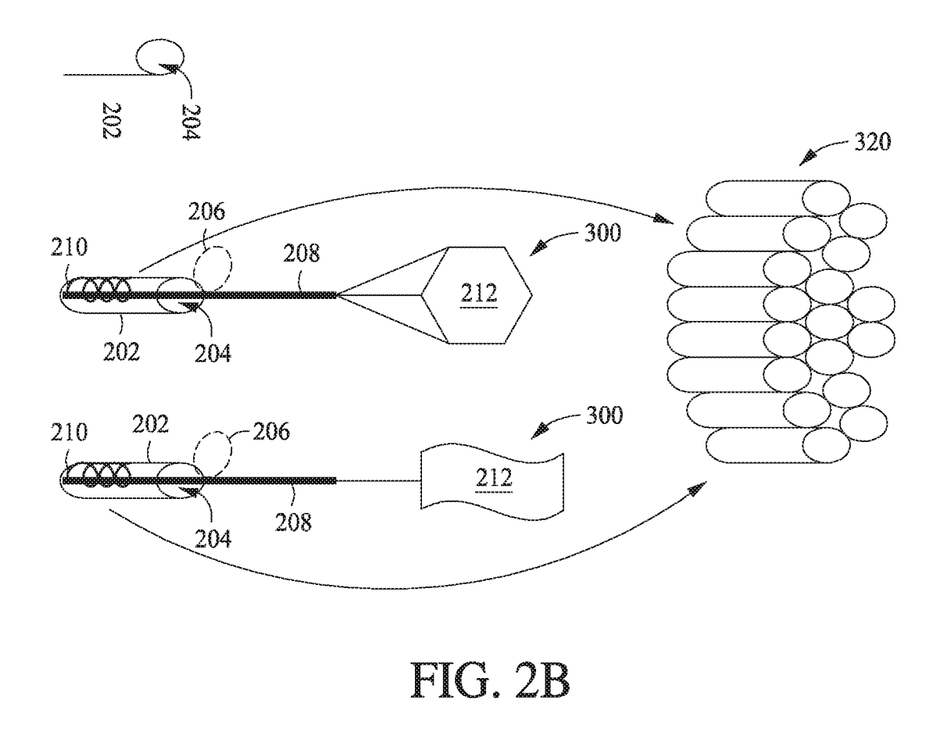
FIG. 2B is an embodiment of an oil camera comprising a housing, a film advance system, a shutter system, and a control system, in accordance with one or more embodiments of the present disclosure.

Referring now to FIG. 1A, illustrated is an embodiment of an oil camera comprising a housing, a film advance system, and a control system, in accordance with one or more embodiments of the present disclosure. Oil camera 100 comprises housing 102, film advance system comprised of spools 104a, 104b, and 104c, and a control system (FIGS. 2A and 2B). The shape of the housing 102 is not considered to be particularly limited and may be cylindrical, ovoid, triangular, polygonal, or otherwise irregular in shape, without departing from the scope of the present disclosure. The housing comprises an opening 102a to expose oleophilic film 106. Further, the housing 102 has integrated therewith the film advance system 104a, 104b, and 104c; that is, the housing 102 may have mounts or other attachment mechanisms to hold spools 104a, 104b, and 104c in place to allow exposure and isolation of film 106, as described in greater detail with reference to FIG. 1B. It is to be appreciated that the housing 102 is shown in phantom to permit visualization of the interior of the housing 102, but is a solid enclosure that isolates all interior elements within the housing 102, except for the exposed film 106 through the opening 102a. As shown, the oil camera 100 is mounted to the side of a deployment platform 110 (only a representative portion shown), which may be a glider, float, vehicle, or other conveyance for deploying the oil camera 100 into an environment of interest.

The magnified portion of FIG. 1A shows an embodiment for isolating the film 106 within the housing 102 when it is not exposed to an environment through opening 102a. As shown, such isolation may be achieved by a double-walled opening in the housing that has isolation rollers 108 which permit the film 106 to feed through, but largely prevent the external environment (e.g., surrounding marine water) from entering into the interior of the housing 102. Other suitable mechanisms may be used for isolating the interior components of the housing 102, while allowing the film 106 to be exposed to an environment of interest, without departing from the scope of the present disclosure.

Figure 1B:
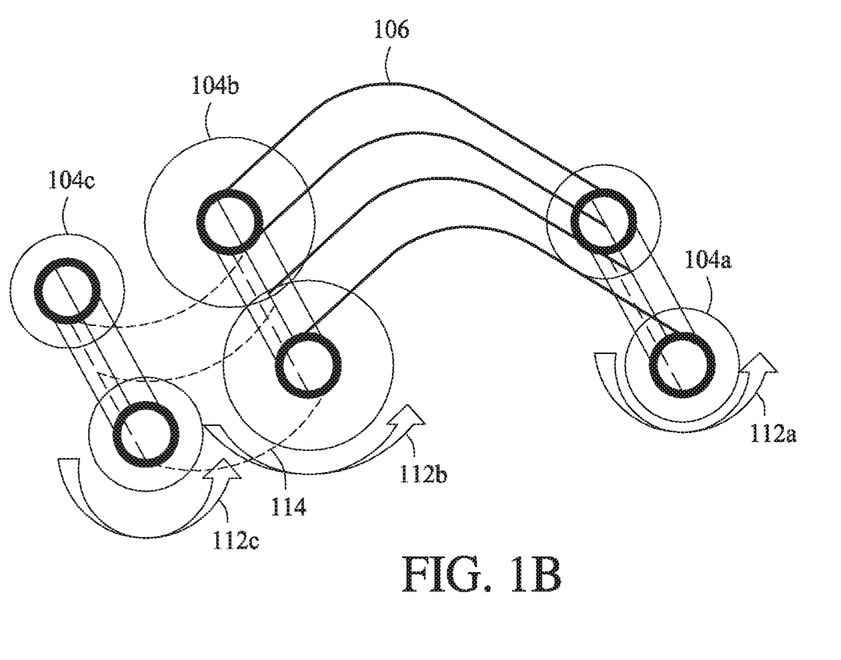
FIG. 1B illustrates the interior of the oil camera of FIG. 1A.

Referring now to FIG. 1B, illustrated is a close up of the interior of the oil camera 100 of FIG. 1A, absent the housing. The film advance system comprised of spools 104a, 104b, and 104c, is advanced using a control system, represented by the arrows 112a, 112b, and 112c. As shown, the film 106 is held between spools 104a and 104b. The edges, or perimeter portions of the film 106, is associated with or otherwise formed of stiffened or thickened feed strips compared to the interior, primary portion of the film 106. As described above, the film 106 is typically thin and the thicker exterior feed strips allow the film advance system and control system to cooperatively advance the film 106 without stressing, tearing, or otherwise interfering negatively with the film 106 material. In addition to film 106, isolation material 114 forms a portion of the oil camera 100 in order to isolate various exposed film frames. The isolation material 114 may be any material capable of isolating film frames and preventing diffusion of sampled compounds between each frame, and may further include a biological-control, as described hereinabove.

In operation, film 106 spools from spool 104a to 104b to expose a film frame. After exposure, the exposed film frame is further spooled onto spool 104b simultaneously with isolation material 114, which is pulled from spool 104c. That is, the unexposed film 106 resides on spool 104a and the uncoupled isolation material 106 resides on spool 104c. After exposure, the exposed film is coupled with the isolation material to isolate the frame from subsequent film frames. The control system 112a, 112b, 112c may be a drive mechanism, belt-feed mechanism between each spool, or other mechanical or electrical mechanism for rotating the film advance system. It will be appreciated that in some embodiments, 112b forms the entirety of control system 112b, or any combination of 112b with 112a and/or 112c, without departing from the scope of the present disclosure.

As shown, during exposure to an environment of interest through opening 102a (FIG. 1A), the film 106 between the two spools 104a, 104b may be slack (rather than taut between the two spools) in order to increase the surface area of the film exposed to the environment. The stiffened feed strips may further facilitate maximizing surface area exposure by providing a semi-rigid perimeter for the film to form an arc, as shown in FIG. 1A, and FIG. 1B.

Referring now to FIG. 2A, illustrated is another embodiment of an oil camera comprising a housing, a film advance system, a shutter system, and a control system, in accordance with one or more embodiments of the present disclosure. Two embodiments of single-use, vertically mountable oil cameras 200 are shown in FIG. 2A. The oil cameras 200 comprise a housing 202, a shutter system comprising a shutter opening 204, and a shutter blade 206 (shown in the open position), a film advance system 208, and a control system 210. As shown, the housing 202 is cylindrical in form, but may be any other suitable elongated shape, without departing from the scope of the present disclosure. Integrated with the housing 202, a shutter system comprises a shutter blade 206 which has an open position (as shown) and a closed position to close the shutter opening 204 and prevent exposure of the interior of the housing 202 to an external environment (e.g., a marine water environment). As shown, a spring-loaded type control system 210 may be used to deploy the film advance system 208, in which the shutter blade 206 opens to expose the shutter opening 208 through which the film advance system 208 advances film 212. The control system 210 may electrically or mechanically operate the shutter blade 206 (e.g., electrical latching or mechanical hinging upon contact and no-contact with the film advance system 208). The control system 210 is shown as a spring-loaded type mechanism, but it may be any mechanism that can advance and retract the film advance system 208 (e.g., a screw or solenoid mechanism), which may further be telescopically extendable or otherwise merely movable (without extension) within the housing 202 into and out of the shutter opening 204.

Prior to deployment, the control system 210 spring is retracted and the film advance system 208 and film 212 are housed within the housing 202 with the shutter blade 206 sealing the shutter opening 204. The film 212 may be spooled or otherwise wrapped around the film advance system prior to deployment. Similarly, after exposure of the film 212, the control system 210 retracts the spring (or other mechanism) to cause the film advance system 208 to retract into the housing 202 and the shutter blade 206 is controlled by the control system 210 or by another suitable mechanism (latch, spring-loaded hinge, etc.) to enter into a closed position to seal the shutter opening 204. The shutter blade 206 may be equipped with an O-ring or similar water-tight sealing mechanism to ensure isolation of the interior of the housing 202 from the environment. In some embodiments, the control system 210 may cause the film advance system 208 to rotate prior to or during retraction after exposure of the film 212 to again spool or otherwise wrap the film 212 around the film advance system. In some embodiments, the housing 202 or a component thereof may comprise a biocide or other biological-control that is exposed to the retracted film 212 after exposure.

As shown, the film 212 may be of various shapes and sizes. In one embodiment, rods or other supports may attach the film 212 to the film advance system (as shown with reference to the hexagonal-shaped film in FIG. 2A). These rods or supports may retract when the film advance system 208 retracts from the housing 202 to stabilize the film 212 in an open position to facilitate maximum exposure to the surrounding environment. Such supports may be particularly useful if the oil camera 200 is used on a deployment platform that is moored. After exposure, the rods or supports retract back into the housing 202 with the film advance system 208 and the exposed film 212. In other embodiments, no rods or supports are used and the film 212 is held in place directly by the film advance system 208 (as shown with reference to the flag-shaped film in FIG. 2A).

The vertical oil cameras 200 of FIG. 2A may be preferably mounted to a deployment platform on its lateral or dorsal side, but may be mounted in any other location on a deployment platform, depending on the type of deployment platform and the type of sampling expected. The vertical oil cameras 200 may be deployed individually in an environment of interest (e.g., only one mounted on a deployment platform), or may otherwise be present in a plurality 220 such that multiple individual exposures from the plurality of oil cameras may be obtained in one or more environments of interest. In some instances, for example, the plurality of oil cameras may be mounted on a belt-feed mechanism, which may be used to rotate an unused oil camera 200 to a sampling location and rotate out a used oil camera 200 from said location. In other embodiments, each oil camera 200 in the plurality of oil cameras 230 may remain stationary (e.g., not change location with reference to a deployment platform).

FIG. 2B illustrates two embodiments of single-use, horizontally mountable oil cameras 300. The horizontal oil cameras are similar in design to the vertical oil cameras 200 of FIG. 2A, hence like functionality and operation will not be again described in detail with reference to the horizontal oil cameras 300 and duplicative reference numbers for the components of FIG. 2A will be repeated in FIG. 2B. Oil cameras 300 in FIG. 2B differ from those in FIG. 2A not in operation, but orientation and thus certain design features. The horizontal oil cameras 300 may be preferably mounted to a deployment platform (not shown in FIG. 2B) on its dorsal (or back) side. When the deployment platform is moving in a direction parallel to the seabed, these horizontal oil cameras 300 may naturally encounter water flow and thus maximum surface area exposure for sampling. However, when the deployment platform is moored, for example, the oil cameras 300 may experience little or no water flow, thus requiring rods or supports that retract with the film advance system 208, regardless of the shape of the film 212. This is because unlike the vertical film advance system 208 of FIG.

2A, which can directly support certain film 212 shapes, the horizontal film advance system 208 of FIG. 2B cannot Like the rods or supports described with reference to FIG. 2A, they may retract upon advancement of the film advance system 212 to permit increased surface area exposure of the film 212 and detract upon retraction of the film advancement system 208 after exposure to the film 212. The film 212 of the horizontal oil cameras 300 may be folded lengthwise prior to and after exposure within the housing 202. Moreover, like the vertical oil cameras 200, the horizontal oil cameras 300 may be deployed singly or as a plurality 320.

The various embodiments of the present disclosure further provide for methods of using the oil cameras described herein, whether configured for single exposure or multiple-exposure. In particular, the oil cameras of the present disclosure may be utilized in order to detect low or ultra-low concentrations of hydrocarbons in a water source (e.g., a marine environment). Various methods may be employed and are based, at least in part, upon the environment being sampled, the deployment platform selected, exposure time (and optimization thereof), the film type selected, and the like, and any combination thereof.

As described hereinabove, the oleophilic film materials used in the embodiments of the present disclosure provide a chemical reservoir for scavenging hydrocarbons from an external environment, such as a water source. In such instances, when water with dissolved hydrocarbons comes into contact with the oleophilic film, the hydrocarbons partition between the water and the film based on their chemical affinity. For this reason, the selected film is oleophilic in nature, such that the hydrocarbons partition into the film (i.e., hydrocarbon affinity for the oleophilic film is one or more orders of magnitude greater than water). The equilibrium partitioning of hydrocarbons from water and into the oleophilic film is accordingly dependent on the type and period of time of exposure of the film. Care must be taken to avoid exposure of the film to environments having lower concentrations of hydrocarbons compared to the concentration already scavenged by an exposed film frame, or else the hydrocarbons will desorb from the film back into the water. For this reason, each exposed film frame is isolated from the water environment, as described above, and highlights the importance of the method of determining the exposure time.

For instance, in any or all embodiments, the present disclosure provides an oil camera as described herein equipped with a methane sensor, fluorometer, and/or other in situ detection sensor and the exposure time of the one or more oleophilic film frames is based in part or entirely on input from one or more of these sensors. In some embodiments the sensor(s) may supply output directly to a processing unit associated with the oil camera as a means of providing the oil camera with triggering and/or exposure time input. Alternatively, the sensor(s) may supply output to a processing unit associated with a platform and that processing unit may provide triggering and/or exposure time input to the oil camera. For example, upon detection of a potential hydrocarbon source, which may be identified upon detection of methane, for example, at least one oleophilic film frame is exposed to the environment. The film may continue to be exposed to the environment until the sensed methane concentration begins to diminish. In such a way, the scavenged hydrocarbons may be collected by the film without or with minimal desorption.

The oil cameras described herein may be restricted to use within a water column, within interstitial water in sediments, or any combination thereof. The particular sampling environment may govern the requirements of the deployment platform and/or the particular design of the oil camera. For example, use of the oil camera in sediment may require an oil camera configured for excluding particulates from the oleophilic film, an oleophilic film exposure opening, and/or shutter system (e.g., a screen or mesh placed within the shutter opening to prevent particulate contact with the film therebehind). In natural hydrocarbon seepage environments, sediment pore water of hydrocarbons moving through the sediment to a main water source may be evaluated. Moreover, if hydrocarbon seepage is dispersed over a large area, the pore water may be at or near heavy hydrocarbon saturation, such that liquid oil is present. Accordingly, if the flow of hydrocarbons in a seepage setting is focused or the hydrocarbons are emanating from facilities above the seafloor, for example, use of the oil camera in the water column may be preferred. In general, use of the oil cameras described herein as close to a hydrocarbon source as possible is preferred, such as a marine environment (e.g., the seabed) for natural hydrocarbon seepage and production facilities for hydrocarbon leakage.

The selected platform for deployment of the oil cameras of the present disclosure may be particularly important for ensuring cost effective sampling and/or detection of hydrocarbons. This may be particularly true because the oil cameras described herein may be utilized over long periods of time, where one or more film frames may be exposed to an environment for sampling or detecting hydrocarbons in time periods equal to or greater than an hour and up to one or more days, depending on the particular environment.

Passive or low-powered autonomous deployment platforms may be preferred to high-powered autonomous deployment platforms. For example, a passive or low-powered platform may reduce costs associated with use of the oil cameras, particularly at locations in which the presence of hydrocarbons is unknown. For example, when searching for the presence of hydrocarbons, a deployment platform may search within a first specific location (e.g., in a box pattern, or other pattern) while exposing a first oleophilic film frame, and thereafter be moved to a second specific location while exposing a second oleophilic film frame. A plurality of oleophilic film frames may be exposed at the same or different locations, each separately exposed (i.e., on a frame-by-frame basis). That is, each frame of a plurality of frames may be advanced into an opening for exposure (e.g., a housing or shutter opening) and thereafter isolated from the opening (e.g., the housing or shutter opening), and another frame advanced thereto for subsequent exposure. In such a way, an otherwise unknown source of hydrocarbons may be elucidated. In other environments in which the presence of hydrocarbons is known, a low-powered or a high-powered autonomous deployment platform may be utilized.

In one or all embodiments, the deployment platform may be a buoyancy-driven autonomous underwater glider (AUG), a buoyancy-controlled passive float, or an autonomous benthic vehicle (ABV) (e.g., a rover, crawler, or hopper). In some instances, it may be preferred to utilize a passive float in large water source areas that have no particular priority target, such as when it is unknown where or if any hydrocarbons of interest are present. Such floats may be utilized to expose the oleophilic film within the oil camera at fixed depths, generally close to the seabed floor, and then return to shallow water where faster currents can move the floats to other (and new) sampling environments. AUGs may be utilized to sample or detect hydrocarbons using the oil cameras of the present disclosure at locations that are more well-defined, such as locations in which hydrocarbons are expected to be present. Further, AUGs may be used in locations for monitoring facilities where leakage may occur at elevations not well suited for ABVs. Additionally, AUGs may be capable of being bottomed and thus well suited to sample interstitial water in sediment. ABVs may be best suited for sampling and/or detecting hydrocarbons over a well-defined target area where the hydrocarbon source is at or near the seabed floor.

In some embodiments, rather than deploying a transport glider, float, or vehicle, the oil cameras of the present disclosure may be deployed using merely a weighted conveyance. The oil camera may be placed at a location within a water column utilizing the weighted conveyance and thereafter detached from the weighted conveyance and allowed to buoyantly rise to the surface, providing the ability to sample the entirety of the water column and/or ease recovery of the oil camera. Moreover, the weighted conveyance may allow fixed location samples throughout the water column, where it is configured to raise the oil camera to the service at fixed depth intervals.

Accordingly, the oil cameras described herein may be allowed to move with the current of a water source while one or more oleophilic film frames are exposed. Alternatively, the oil cameras may be held static at a particular location within a water source and thereafter moved to a second particular location, and so on. Moreover, in addition to or alternatively with a methane sensor, for example, the deployment platform selected may be equipped with one or more means of locating hydrocarbons (e.g., seepage). For example, the deployment platform may be equipped with a multibeam echosounder, side-scan sonar, X-band radar, and the like, and any combination thereof.

Based on the foregoing, therefore, the present disclosure provides a method for optimizing the use of one or more oil cameras described herein for the detection and/or sampling of hydrocarbons, particularly in an underwater or submarine environment. An optimal sampling environment is selected based on the need to detect and/or sample hydrocarbons. Such environment may include a water column, interstitial water in sediment, or a combination thereof. That is, deployment of a particular oil camera may be utilized in more than one type of environment. A deployment platform is additionally selected for deploying the oil camera to the environment of interest. Selection of the deployment platform may be based at least upon one or more of the selected environment, the expected hydrocarbon type and concentration in the environment, and the sampling requirements extending therefrom. The oleophilic film selected for use in the oil camera may additionally be selected based on one or more of the sampling goals, compatibility with the environment and expected hydrocarbon type and concentration, time available for sampling, and the like, and any combination thereof. Additionally, the methods described herein include determining or defining an exposure time for at least one frame of the oleophilic film using a pre-specified amount of time given the environment selected and/or based on sensor input from a sensor used in concert with the oil camera (e.g., a methane sensor, a fluorometer, and the like, and any combination thereof).

In addition, the present disclosure provides a means of optimizing post-analysis of the hydrocarbons scavenged using the oleophilic film of the deployed oil cameras described herein. Detection of hydrocarbon molecules, as defined herein (i.e., with ≥6 carbon atoms), particularly those released into natural water sources (e.g., due to natural seepage), may be challenged by their general limited solubility in water and by substantial dilution. Solubility of molecular families of crude oil, such as n-alkanes or aromatic compounds, decreases as their carbon content (and, thus size) increases, as well as with an increasing number of rings. For example, benzene ($C_6H_6$, having one ring) is more soluble than naphthalene ($C_{10}H_8$, having two rings); naphthalene is more soluble than phenanthrene ($C_{14}H_{10}$, having three rings); and phenalthrene is more soluble than pyrene ($C_{16}H_{10}$, having four rings). This same sequence also describes the relative abundance of the multi-ring aromatic molecules in medium weight crude oil (i.e., greater amount of naphthalene compared to the higher hydrocarbon molecules, while benzene concentrations are more variable but typically most comparable to naphthalene concentrations). Accordingly, the most abundant hydrocarbon molecules are the most soluble, and thus the best targets for identifying the presence of crude oil in an environment (e.g., water or sediment) using the oil cameras described herein.

Certain biomarkers may be disposed within crude oil and used to determine various insights about the nature of the oil, such as its thermal maturity and rock type. These biomarkers are only slightly modified from their biological precursors and provide valuable source information about crude oil origins. However, such biomarkers are typically only in low concentrations within the oil and relatively insoluble in water.

As described hereinabove, detecting or sampling environments for the presence of hydrocarbons using the oil camera(s) of the present disclosure operate by scavenging and concentrating hydrocarbon molecules into an oleophilic film material. Such hydrocarbon molecules may be scavenged from an environment, such as a water column, proportional to their concentration therein and to the partition coefficient of the particular hydrocarbon molecule between the water and the film material. In general, the more insoluble a hydrocarbon molecule is, the more strongly it will partition to the oleophilic film materials described herein. Thus, typically the concentrations of compounds scavenged by the film of the oil camera(s) described herein represent the most abundant, and most soluble hydrocarbon molecules found in crude oil. Accordingly, based on the expected composition of a crude oil and its expected solubility in water, the concentration of hydrocarbon molecules scavenged by a particular oleophilic film material over a particular period of time may be estimated using one or more models based on source proximity, dilution, and loss. Such estimates may be further improved with laboratory testing of the exposed oleophilic film material.

One or several post-analysis approaches may be utilized alone or in combination to extract and analyze hydrocarbon molecules scavenged by one or more exposed oleophilic film frames of the present disclosure.

In one or all instances, for example, the hydrocarbon molecules may be stripped or otherwise removed (e.g., chemically desorbed) from the exposed film using one or more solvents. The hydrocarbon molecules may be concentrated within the solvent to further improve analysis. Alternatively, the hydrocarbon molecules may be sequentially liberated from the film, such as by thermal desorption, and introduced directly into an analytical machine (e.g., thermal desorption GC-MS). During thermal desorption, the molecules may be sequentially liberated based on relative thermal volatility. In any or all instances, the entirety of one or more exposed film frames may be chemically stripped or thermally desorbed and the resultant product analyzed using an analytical machine. Rather than destructively analyzing exposed film, the film may alternatively or additionally first be analyzed using a non-destructive technique, such as fluorometry.

The particular post-analysis preparation and analysis technique selected may favor detection of certain hydrocarbon molecules over others, or may prevent further testing (e.g., if a destructive technique is selected). Accordingly, a combination of post-analysis techniques may be preferred to glean the most accurate information regarding the crude oil concentration and type scavenged by the exposed film material. Moreover, certain techniques may be prioritized to maximize the information obtained (e.g., non-destructive techniques before destructive techniques).

In some embodiments, the present disclosure provides a method of sampling an environment using the oil camera(s) described herein and, thereafter, ranking a set of related exposed oleophilic film frames based on their likelihood of having sufficient concentrations of one or more hydrocarbon molecules to allow useful analysis. The ranked samples may then be processed using an optimal combination of optional pre-concentration steps and analytical techniques. The particular ranking selected may be based on an ultimate goal of assuring that the exposed film material is analyzed to obtain information about hydrocarbon molecules that are considered to be most valuable, such as of the greatest downstream value. If such data cannot be obtained from one or more exposed film frames, such frames may be analyzed for hydrocarbon molecules that will yield the most information. By such ranking, the likelihood of destroying exposed film frames having hydrocarbon molecule concentrations of interest and that can be usefully detected may be minimized. For example, exposed films may be initially tested non-destructively to determine which are of greater likelihood to yield information of interest and, thereafter, destructive techniques may be used on only those lesser ranked exposed films (e.g., those with the lowest concentration of accumulated hydrocarbons), or first used on only those lesser ranked exposed films.

In any or all embodiments, the post-analysis ranking may be based on one or more sources of information. For example, during hydrocarbon molecule scavenging using the oleophilic film and oil camera(s) described herein, direct information on the potential for successfully collecting such molecules may be determined by in situ information (e.g., a methane sensor, a fluorometer, and/or other scanning or radar methods previously discussed). When such in situ sensors indicate high or relatively high levels of hydrocarbon molecules in a particular environment, exposed film frame(s) sampling in that environment may be ranked relatively high. This high ranking is based on the higher likelihood that high concentrations of hydrocarbon molecules of interest are likely present in such films. Indirect information may additionally be utilized to rank exposed film frames for post-analysis. For example, indirect evidence based on solubility and the solution-retention potential of hydrocarbon molecules may be used. Such indirect evidence may be dependent on a number of factors, such as temperature, salinity, turbidity, and the like, and any combination thereof, for example. Ranking may further be established using non-destructive testing (e.g., fluoroscopic analysis) in the field at the time of collection or in a laboratory setting in order to initially determine the likelihood of exposed films having the most valuable information regarding hydrocarbon content and/or concentration (e.g., having biomarkers present). Validation of a particular ranking process may be achieved by analysis of various exposed films being suitable for the desired post-analysis technique(s). Additionally, initial determination or prediction of the type and concentration of hydrocarbon molecules (e.g., larger molecules may fluoresce more strongly) may dictate the particular post-analysis technique(s) most suitable.

Accordingly, in any or all embodiments, the exposed oleophilic film frame(s) may be optimized for analysis to detect hydrocarbons in an environment of interest, such as a water column or interstitial water in sediment. The optimization method may include deploying an oil camera according to one or more embodiments of the present disclosure to an environment of interest, exposing one or more oleophilic film frames to the environment, and ranking the exposed one or more oleophilic film frames based on likely hydrocarbon type and/or concentration to determine preferred or more valuable candidate frames for analysis. The ranking may be based, for example, on selection of exposed film frames having the least abundant suite of hydrocarbon molecules of interest, such as the biomarkers described hereinabove. Such frames would be ranked of high value. Lesser ranked frames may comprise only hydrocarbon molecules of lesser value or interest, such as more highly soluble hydrocarbons.

The ranking may be achieved using pre-screening methods (e.g., fluoroscopic analysis), data collected during film exposure (e.g., methane or other sensor information), and the like, and any combination thereof. In any or all instances, sub-sampling of one or more of the exposed film frames may additionally be performed to allow for multiple analyses and conducting of initial analyses of the molecules that are expected to be most abundant in the exposed film (e.g., more soluble hydrocarbon molecules) to obtain further information. That is, the exposed film of potentially less value (e.g., potentially lacking desirable biomarkers) may first be tested, including by destructive means, to determine the efficacy of a selected post-analysis technique.

After ranking the exposed film frames as described, post-analysis of the ranked frames and/or grouping of ranking frames may be carried out using a selected post-analysis method that is most likely to yield the greatest amount of information about the hydrocarbon molecules present. The rankings of the frames and/or grouping of ranked frames may be thereafter adjusted, if needed, based on data received. Such post-analysis methods may include, but are not limited to, fluorescence analysis, thermal desorption, chemical desorption, flame detection, GC-MS, GC-MS/MS, and the like, and any combination thereof. Selection of one or more methods may be based on a number of factors. For example, fluorescence analysis may be achieved without destroying the frame sample.

Chemical stripping or desorption of the film may be a desirable option for testing a sample part of a piece of film to verify, for example, in situ results and/or non-destructive laboratory testing results. Chemical desorption may also be a desirable approach for films that are believed to host significant quantities of more thermal refractive molecules that cannot be effectively thermally desorbed. In other examples, detection of molecules in solvents may be accomplished for bulk analyses most readily by GC-FID or GC-MS. Determination of larger molecules, especially biomarkers, may be most readily accomplished using either chemical or thermal desorption and GC-MS/MS.

Therefore, the present disclosure provides embodiments of an oil camera apparatus and system for exposing oleophilic film to an environment of interest for sampling or detecting hydrocarbon molecules; a method of deploying such oil camera; and methods of ranking the exposed film for optimizing the analysis of the exposed film.

One or more illustrative embodiments incorporating the embodiments disclosed herein are presented. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related, and other constraints, which vary by implementation and from time to time. While a developer's efforts might be time-consuming, such efforts would be, nevertheless, a routine undertaking for those of ordinary skill in the art and having benefit of this disclosure.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

While compositions and methods are described herein in terms of "comprising" various components or steps, the compositions and methods can also "consist essentially of" or "consist of" the various components and steps.

Embodiments disclosed herein include:

Embodiment A: An apparatus comprising: a housing; a shutter system disposed within the housing, the shutter system comprising: a shutter opening configured to expose at least a first frame of oleophilic film, and a shutter blade configured to move the shutter opening between an open position to expose both the shutter opening and the first frame and a closed position to cover the shutter opening; a film advance system integrated with the housing and configured to advance the first frame into the shutter opening; and a control system configured to control one or both of the shutter system and the film advance system.

Embodiment A may have one or more of the following additional elements in any combination:

Element A1: Wherein the control system is configured for remote control of one or both of the shutter system and the film advance system.

Element A2: Wherein the shutter blade forms a fluid-tight seal of the shutter opening when in the closed position.

Element A3: Wherein the oleophilic film is selected from the group consisting of polydimethylsiloxane, poly(imino (1,6-dioxo-1,6-hexanediyl)imino-1,6-hexanediyl), polytetrafluoroethylene, polypropylene cloth, polyethylene, low-density polyethylene, and any combination thereof.

Element A4: Further comprising a methane sensor in electrical communication with the apparatus.

Element A5: Wherein the film advance system comprises a film carrousel or a film spool.

Element A6: Wherein the film advance system moves the shutter blade between the open position and the closed position.

Element A7: Wherein the film advance system is further configured to advance and isolate the first frame after the first frame is exposed.

Element A8: Wherein the film advance system is further configured to advance and isolate the first frame after the first frame is exposed, and wherein the oleophilic film comprises the first frame and at least a second frame, and the film advance system is further configured to advance the second frame into the shutter opening after or simultaneously with advancing and isolating the first frame after the first frame is exposed.

Element A9: Wherein the film advance system is further configured to advance and isolate the first frame after the first frame is exposed, wherein the oleophilic film comprises the first frame and at least a second frame, and the film advance system is further configured to advance the second frame into the shutter opening after or simultaneously with advancing and isolating the first frame after the first frame is exposed, and wherein the oleophilic film is in the form of a linear array, a two-dimensional array, or a three-dimensional array.

By way of non-limiting example, exemplary combinations applicable to Embodiment A include: A1 and A2; A1 and A3; A1 and A4; A1 and A5; A1 and A6; A1 and A7; A1 and A8; A1 and A9; A2 and A3; A2 and A4; A2 and A5; A2 and A6; A2 and A7; A2 and A8; A2 and A9; A3 and A4; A3 and A5; A3 and A6; A3 and A7; A3 and A8; A3 and A9; A4 and A5; A4 and A6; A4 and A7; A4 and A8; A4 and A9; A5 and A6; A5 and A7; A5 and A8; A5 and A9; A6 and A7; A6 and A8; A6 and A9; A7 and A8; A7 and A9; A8 and A9; and any non-limiting combination of one, more, or all of A1, A2, A3, A4, A5, A6, A7, A8, and/or A9.

Embodiment B: A method comprising: deploying the apparatus according to Embodiment A and any non-limiting combination of none, one, more, or all of Elements A1-A9 into an environment; and exposing at least the first frame to the environment.

Embodiment B may have one or more of the following additional elements in any combination:

Element B1: Wherein the environment is one or both of a water column and interstitial water in sediment.

Element B2: Wherein the environment is one or both of a water column and interstitial water in sediment, and wherein the water column and sediment are located in a marine setting.

Element B3: Further comprising deploying the apparatus into the environment using a deployment platform.

Element B4: Further comprising deploying the apparatus into the environment using a deployment platform, and wherein the deployment platform comprises a buoyancy-driven autonomous underwater glider, a buoyancy-controlled passive float, an autonomous benthic vehicle, or a weighted conveyance.

Element B5: Wherein exposing at least the first frame to the environment is for a defined period of time.

Element B6: Further comprising selecting the oleophilic film based on potentially present hydrocarbons in the environment.

Element B7: Further comprising analyzing the exposed first frame to determine the presence or absence of hydrocarbons present in the environment.

Element B8: Further comprising analyzing the exposed first frame to determine the presence or absence of hydrocarbons present in the environment, and wherein performing the analyzing comprises using a technique selected from the group consisting of fluorescence analysis, thermal desorption, chemical desorption, flame detection, gas chromatograph mass spectrometry, gas chromatograph tandem mass spectrometry, and any combination thereof.

By way of non-limiting example, exemplary combinations applicable to Embodiment B include: B1 and B2; B1 and B3; B1 and B4; B1 and B5; B1 and B6; B1 and B7; B1 and B8; B2 and B3; B2 and B4; B2 and B5; B2 and B6; B2 and B7; B2 and B8; B3 and B4; B3 and B5; B3 and B6; B3 and B7; B3 and B8; B4 and B5; B4 and B6; B4 and B7; B4 and B8; B5 and B6; B5 and B7; B5 and B8; B6 and B7; B6 and B8; B7 and B8; and any non-limiting combination of one, more, or all of B1, B2, B3, B4, B5, B6, B7, and/or B8.

Embodiment C: An apparatus comprising: a housing; a shutter system disposed within the housing, the shutter system comprising: a shutter opening configured to expose a plurality of oleophilic film frames, and a shutter blade configured to move the shutter opening between an open position to expose both the shutter opening and the plurality of oleophilic film frames and a closed position to cover the shutter opening; a film advance system integrated with the housing and configured to advance the plurality of oleophilic film frames into the shutter opening; and a control system configured to control one or both of the shutter system and the film advance system.

Embodiment C may have one or more of the following additional elements in any combination:

Element C1: Wherein the control system is configured for remote control of one or both of the shutter system and the film advance system.

Element C2: Wherein the shutter blade forms a fluid-tight seal of the shutter opening when in the closed position.

Element C3: Wherein the plurality of oleophilic film frames are selected from the group consisting of polydimethylsiloxane, poly(imino(1,6-dioxo-1,6-hexanediyl)imino-1,6-hexanediyl), polytetrafluoroethylene, polypropylene cloth, polyethylene, low-density polyethylene, and any combination thereof.

Element C4: Further comprising a methane sensor in electrical communication with the apparatus.

Element C5: Wherein the film advance system comprises a film carrousel or a film spool.

Element C6: Wherein the film advance system moves the shutter blade between the open position and the closed position.

Element C7: Wherein the film advance system is further configured to advance and isolate the plurality of oleophilic film frames into the shutter opening and out of the shutter opening on a frame-by-frame basis.

Element C8: Wherein the plurality of oleophilic film frames are in the form of a linear array, a two-dimensional array, or a three-dimensional array.

By way of non-limiting example, exemplary combinations applicable to Embodiment C include: C1 and C2; C1 and C3; C1 and C4; C1 and C5; C1 and C6; C1 and C7; C1 and C8; C2 and C3; C2 and C4; C2 and C5; C2 and C6; C2 and C7; C2 and C8; C3 and C4; C3 and C5; C3 and C6; C3 and C7; C3 and C8; C4 and C5; C4 and C6; C4 and C7; C4 and C8; C5 and C6; C5 and C7; C5 and C8; C6 and C7; C6 and C8; C7 and C8; and any non-limiting combination of one, more, or all of C1, C2, C3, C4, C5, C6, C7, and/or C8.

Embodiment D: A method comprising: deploying the apparatus according to Embodiment C and any non-limiting combination of none, one, more, or all of Elements C1-C8 into an environment; and exposing at least the first frame to the environment.

Embodiment D may have one or more of the following additional elements in any combination:

Element D1: Wherein the environment is one or both of a water column and interstitial water in sediment.

Element D2: Wherein the environment is one or both of a water column and interstitial water in sediment, and wherein the water column and sediment are located in a marine setting.

Element D3: Further comprising deploying the apparatus into the environment using a deployment platform.

Element D4: Further comprising deploying the apparatus into the environment using a deployment platform, and wherein the deployment platform comprises a buoyancy-driven autonomous underwater glider, a buoyancy-controlled passive float, an autonomous benthic vehicle, or a weighted conveyance.

Element D5: Wherein separately exposing the plurality of oleophilic film frames to the environment is each for a defined period of time.

Element D6: Further comprising selecting the oleophilic film based on potentially present hydrocarbons in the environment.

Element D7: Further comprising analyzing the exposed plurality of oleophilic film frames to determine the presence or absence of hydrocarbons present in the environment.

Element D8: Further comprising analyzing the exposed plurality of oleophilic film frames to determine the presence or absence of hydrocarbons present in the environment, and wherein performing the analyzing comprises using a technique selected from the group consisting of fluorescence analysis, thermal desorption, chemical desorption, flame detection, gas chromatograph mass spectrometry, gas chromatograph tandem mass spectrometry, and any combination thereof.

Element D9: Further comprising analyzing the exposed plurality of oleophilic film frames to determine the presence or absence of hydrocarbons present in the environment, and value ranking the exposed plurality of oleophilic film frames prior to the analyzing, wherein a highest value ranking is based on the likelihood of the presence of hydrocarbon biomarkers.

Element D10: Further comprising analyzing the exposed plurality of oleophilic film frames to determine the presence or absence of hydrocarbons present in the environment, value ranking the exposed plurality of oleophilic film frames prior to the analyzing, wherein a highest value ranking is based on the likelihood of the presence of hydrocarbon biomarkers, and wherein the ranking is based on non-destructive analysis.

Element D11: Further comprising analyzing the exposed plurality of oleophilic film frames to determine the presence or absence of hydrocarbons present in the environment, value ranking the exposed plurality of oleophilic film frames prior to the analyzing, wherein a highest value ranking is based on the likelihood of the presence of hydrocarbon biomarkers, and wherein the ranking is based on non-destructive analysis comprising fluorescence analysis, methane sensor analysis, and any combination thereof.

Element D12: Further comprising analyzing the exposed plurality of oleophilic film frames to determine the presence or absence of hydrocarbons present in the environment, value ranking the exposed plurality of oleophilic film frames prior to the analyzing, wherein a highest value ranking is based on the likelihood of the presence of hydrocarbon biomarkers, and wherein the ranking is based on non-destructive analysis and a lowest value ranking is based on the lowest concentration of accumulated hydrocarbon molecules.

Element D13: Further comprising analyzing the exposed plurality of oleophilic film frames to determine the presence or absence of hydrocarbons present in the environment, value ranking the exposed plurality of oleophilic film frames prior to the analyzing, wherein a highest value ranking is based on the likelihood of the presence of hydrocarbon biomarkers, and wherein the ranking is based on non-destructive analysis and a lowest value ranking is based on the lowest concentration of accumulated hydrocarbon molecules, and further comprising analyzing the lowest value ranked exposed plurality of oleophilic film frames prior to analyzing the highest value ranked exposed plurality of oleophilic film frames.

By way of non-limiting example, exemplary combinations applicable to Embodiment D include: D1 and D2; D1 and D3; D1 and D4; D1 and D5; D1 and D6; D1 and D7; D1 and D8; D1 and D9; D1 and D10; D1 and D11; D1 and D12; D1 and D13; D2 and D3; D2 and D4; D2 and D5; D2 and D6; D2 and D7; D2 and D8; D2 and D9; D2 and D10; D2 and D11; D2 and D12; D2 and D13; D3 and D4; D3 and D5; D3 and D6; D3 and D7; D3 and D8; D3 and D9; D3 and D10; D3 and D11; D3 and D12; D3 and D13; D4 and D5; D4 and D6; D4 and D7; D4 and D8; D4 and D9; D4 and D10; D4 and D11; D4 and D12; D4 and D13; D5 and D6; D5 and D7; D5 and D8; D5 and D9; D5 and D10; D5 and D11; D5 and D12; D5 and D13; D6 and D7; D6 and D8; D6 and D9; D6 and D10; D6 and D11; D6 and D12; D6 and D13; D7 and D8; D7 and D9; D7 and D10; D7 and D11; D7 and D12; D7 and D13; D8 and D9; D8 and D10; D8 and D11; D8 and D12; D8 and D13; D9 and D10; D9 and D11; D9 and D12; D9 and D13; D10 and D11; D10 and D12; D10 and D13; D11 and D12; D11 and D13; D12 and D13; and any non-limiting combination of one, more, or all of D1, D2, D3, D4, D5, D6, D7, D8, D9, D10, D11, D12, and/or D13.

Embodiment E: An apparatus comprising: a housing; a shutter system disposed within the housing, the shutter system comprising: a shutter opening configured to expose at a frame of oleophilic film, and a shutter blade configured to move the shutter opening between an open position to expose both the shutter opening and the frame and a closed position to cover the shutter opening; and a control system configured to control the shutter system.

Embodiment E may have one or more of the following additional elements in any combination:

Element E1: Wherein the control system is configured for remote control of the shutter system.

Element E2: Wherein the shutter blade forms a fluid-tight seal of the shutter opening when in the closed position.

Element E3: Wherein the oleophilic film is selected from the group consisting of polydimethylsiloxane, poly(imino (1,6-dioxo-1,6-hexanediyl)imino-1,6-hexanediyl), polytetrafluoroethylene, polypropylene cloth, polyethylene, low-density polyethylene, and any combination thereof.

Element E4: Further comprising a methane sensor in electrical communication with the apparatus.

By way of non-limiting example, exemplary combinations applicable to Embodiment E include: E1 and E2; E1 and E3; E1 and E4; E2 and E3; E2 and E4; E3 and E4; and any non-limiting combination of one, more, or all of E1, E2, E3, and/or E4.

Embodiment F: A method comprising: deploying the apparatus according to Embodiment E and any non-limiting combination of none, one, more, or all of Elements E1-E4 into an environment; and exposing at least the frame to the environment.

Embodiment F may have one or more of the following additional elements in any combination:

Element F1: Wherein the environment is one or both of a water column and interstitial water in sediment.

Element F2: Wherein the environment is one or both of a water column and interstitial water in sediment, and wherein the water column and sediment are located in a marine setting.

Element F3: Further comprising deploying the apparatus into the environment using a deployment platform.

Element F4: Further comprising deploying the apparatus into the environment using a deployment platform, and wherein the deployment platform comprises a buoyancy-driven autonomous underwater glider, a buoyancy-controlled passive float, an autonomous benthic vehicle, or a weighted conveyance.

Element F5: Wherein exposing the frame of oleophilic film to the environment is for a defined period of time.

Element F6: Further comprising selecting the oleophilic film based on potentially present hydrocarbons in the environment.

Element F7: Further comprising analyzing the exposed frame to determine the presence or absence of hydrocarbons present in the environment.

Element F8: Further comprising analyzing the exposed frame to determine the presence or absence of hydrocarbons present in the environment, and wherein performing the analyzing comprises using a technique selected from the group consisting of fluorescence analysis, thermal desorption, chemical desorption, flame detection, gas chromatograph mass spectrometry, gas chromatograph tandem mass spectrometry, and any combination thereof.

By way of non-limiting example, exemplary combinations applicable to Embodiment F include: F1 and F2; F1 and F3; F1 and F4; F1 and F5; F1 and F6; F1 and F7; F1 and F8; F2 and F3; F2 and F4; F2 and F5; F2 and F6; F2 and F7; F2 and F8; F3 and F4; F3 and F5; F3 and F6; F3 and F7; F3 and F8; F4 and F5; F4 and F6; F4 and F7; F4 and F8; F5 and F6; F5 and F7; F5 and F8; F6 and F7; F6 and F8; F7 and F8; and any non-limiting combination of one, more, or all of F1, F2, F3, F4, F5, F6, F7, and/or F8.

Embodiment G: An apparatus comprising: a housing; a film advance system integrated with the housing and configured to advance and expose a first frame of oleophilic film; and a control system configured to control the film advance system.

Embodiment G may have one or more of the following additional elements in any combination:

Element G1: Wherein the control system is configured for remote control of the film advance system.

Element G2: Wherein the oleophilic film is selected from the group consisting of polydimethylsiloxane, poly(imino (1,6-dioxo-1,6-hexanediyl)imino-1,6-hexanediyl), polytetrafluoroethylene, and any combination thereof.

Element G3: Further comprising a methane sensor in electrical communication with the apparatus.

Element G4: Wherein the film advance system comprises a film carrousel or a film spool.

Element G5: Wherein the film advance system is further configured to advance and isolate the first frame after the first frame is exposed.

Element G6: Wherein the oleophilic film comprises the first frame and at least a second frame, and wherein the film advance system is further configured to advance and expose the second frame after or simultaneously with advancing and isolating the first frame after the first frame is exposed.

Element G7: Wherein the oleophilic film is in the form of a linear array, a two-dimensional array, or a three-dimensional array.

By way of non-limiting example, exemplary combinations applicable to Embodiment G include: G1 and G2; G1 and G3; G1 and G4; G1 and G5; G1 and G6; G1 and G7; G2 and G3; G2 and G4; G2 and G5; G2 and G6; G2 and G7; G3 and G4; G3 and G5; G3 and G6; G3 and G7; G4 and G5; G4 and G6; G4 and G7; G5 and G6; G5 and G7; G6 and G7; and any non-limiting combination of one, more, or all of G1, G2, G3, G4, G5, G6, and/or G7.

Embodiment H: A method comprising: deploying the apparatus according to Embodiment G and any non-limiting combination of none, one, more, or all of Elements G1-G7 into an environment, wherein when the first frame is advanced and exposed, it is exposed to the environment.

Embodiment H may have one or more of the following additional elements in any combination:

Embodiment H1: Wherein the environment is one or both of a water column and interstitial water in sediment.

Embodiment H2: Wherein the environment is one or both of a water column and interstitial water in sediment, and wherein the water column and sediment are located in a marine setting.

Embodiment H3: Further comprising deploying the apparatus into the environment using a deployment platform.

Embodiment H4: Further comprising deploying the apparatus into the environment using a deployment platform, wherein the deployment platform comprises a buoyancy-driven autonomous underwater glider, a buoyancy-controlled passive float, an autonomous benthic vehicle, or a weighted conveyance.

Embodiment H5: Wherein exposing the first frame to the environment is for a defined period of time.

Embodiment H6: Further comprising selecting the oleophilic film based on potentially present hydrocarbons in the environment.

Embodiment H7: Further comprising analyzing the exposed first frame to determine the presence or absence of hydrocarbons present in the environment.

Embodiment H8: Further comprising analyzing the exposed first frame to determine the presence or absence of hydrocarbons present in the environment, and wherein performing the analyzing comprises using a technique selected from the group consisting of fluorescence analysis, thermal desorption, chemical desorption, flame detection, gas chromatograph mass spectrometry, gas chromatograph tandem mass spectrometry, and any combination thereof.

By way of non-limiting example, exemplary combinations applicable to Embodiment H include: H1 and H2; H1 and H3; H1 and H4; H1 and H5; H1 and H6; H1 and H7; H1 and H8; H2 and H3; H2 and H4; H2 and H5; H2 and H6; H2 and H7; H2 and H8; H3 and H4; H3 and H5; H3 and H6; H3 and H7; H3 and H8; H4 and H5; H4 and H6; H4 and H7; H4 and H8; H5 and H6; H5 and H7; H5 and H8; H6 and H7; H6 and H8; H7 and H8; and any non-limiting combination of one, more, or all of H1, H2, H3, H4, H5, H6, H7, and/or H8.

Therefore, the present disclosure is well adapted to attain the ends and advantages mentioned, as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is, therefore, evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. An apparatus comprising:
a housing;
a film advance system integrated with the housing and configured to move a first frame of oleophilic film:
from inside of the housing through at least one opening of the housing to outside of the housing in order to expose the first frame to an environment external to the housing; and
after exposure from the environment into the housing through the at least one opening of the housing, wherein the film advance system includes a structure to prevent fluid in the environment from entering the at least one opening; and
a control system configured to control the film advance system,
wherein the at least one opening comprises a single opening through which the first frame exits the housing to be exposed to the environment and through which the first frame re-enters the housing after being exposed to the environment.

2. The apparatus of claim 1, wherein the oleophilic film is selected from the group consisting of polydimethyl siloxane, poly(imino(1,6-dioxo-1,6-hexanediyl)imino-1,6-hexanediyl), polytetrafluoroethylene, and any combination thereof.

3. The apparatus of claim 1, further comprising a methane sensor in electrical communication with the apparatus and configured to provide an indication of methane concentration; and
wherein the control system is configured to control exposure of the first frame to the environment external to the housing based on the indication of the methane concentration.

4. The apparatus of claim 1, wherein the film advance system is further configured to advance and isolate the first frame after the first frame is exposed; and
wherein the oleophilic film comprises the first frame and at least a second frame, and wherein the film advance system is further configured to advance and expose the second frame after or simultaneously with advancing and isolating the first frame after the first frame is exposed.

5. The apparatus of claim 1, wherein the structure comprises a shutter that is configured to open so that the first frame exits the single opening and to close so that the first frame is sealed within the housing.

6. The apparatus of claim 5, wherein the film advance system, under control of the control system, is configured to open the shutter, move the first frame from inside the housing through the single opening into the environment in order to expose the first frame to the environment, move the first frame from the environment back through the single opening into the housing, and close the shutter.

7. The apparatus of claim 6, wherein the film advance system includes a rod on which the first frame is attached;
   wherein the rod is configured to extend through the single opening so that the first frame is exposed to the environment; and
   wherein the rod is configured to retract back through the single opening and back into the housing after the first frame is exposed to the environment.

8. The apparatus of claim 7, wherein the control system comprises a spring-type control system that is configured to extend the rod through the single opening and to retract the rod back through the single opening.

9. The apparatus of claim 6, wherein the housing comprising a plurality of housing sections;
   wherein film in each of the plurality of housing sections consists of a single frame of oleophilic film;
   wherein each of the plurality of housing sections includes the shutter; and
   wherein the single frame of oleophilic film from a respective housing section is exposed to the environment by opening a respective shutter and moving the single frame of oleophilic film from the respective housing section into the environment.

10. A method comprising:
    deploying an apparatus to an environment, wherein the apparatus comprises:
       a housing;
       a film advance system integrated with the housing and configured to advance and expose a first frame of oleophilic film; and
       a control system configured to control the film advance system; and
    exposing at least the first frame to the environment by:
       moving the first frame from inside the housing through a single opening to outside the housing in order to expose the first frame to an environment external to the housing; and
       after exposing the first frame to the environment external to the housing, moving the first frame through the single opening so that the first frame is back within the housing, with the film advance system including a structure to prevent fluid in the environment from entering the at least one opening.

11. The method of claim 10, wherein the environment is one or both of a water column and interstitial water in sediment.

12. The method of claim 10, further comprising deploying the apparatus into the environment using a deployment platform.

13. The method of claim 10, further comprising analyzing the exposed first frame to determine presence or absence of hydrocarbons present in the environment.

14. The method of claim 10, wherein prior to moving the first frame through the single opening, a shutter is opened to create the single opening; and
    after the first frame is moved from the environment through the single opening back into the housing, the shutter is closed.

15. The method of claim 14, wherein after opening the shutter to create the single opening, moving a rod, on which the first frame is connected, so that at least a part of the rod moves through the single opening into the environment so that the first frame likewise moves through the single opening into the environment; and
    wherein, after exposure to the environment, the at least a part of the rod moves back through the single opening into the housing so that the first frame likewise moves through the single opening back into the housing.

16. The method of claim 14, wherein the housing comprising a plurality of housing sections;
    wherein film in each of the plurality of housing sections consists of a single frame of oleophilic film;
    wherein each of the plurality of housing sections includes the shutter; and
    wherein the single frame of oleophilic film from a respective housing section is exposed to the environment by opening a respective shutter and moving the single frame of oleophilic film from the respective housing section into the environment.

* * * * *